US012011423B2

(12) United States Patent
Barkan et al.

(10) Patent No.: US 12,011,423 B2
(45) Date of Patent: Jun. 18, 2024

(54) S-ALKYLISOTHIOURONIUM DERIVATIVES FOR TREATING UTERINE HYPERCONTRACTILITY DISORDERS

(71) Applicant: FORAVISET LTD., Jerusalem (IL)

(72) Inventors: Refael Barkan, Rishon le Zion (IL); Victor Ghicavii, Chisinau (MD)

(73) Assignee: Foraviset Ltd., Jerusalem (IL)

( * ) Notice: Subject to any disclaimer, the term of this patent is extended or adjusted under 35 U.S.C. 154(b) by 0 days.

(21) Appl. No.: 16/944,137

(22) Filed: Jul. 30, 2020

(65) Prior Publication Data

US 2020/0360313 A1 Nov. 19, 2020

Related U.S. Application Data

(63) Continuation-in-part of application No. 12/741,759, filed as application No. PCT/IL2008/001466 on Nov. 6, 2008, now abandoned.

(30) Foreign Application Priority Data

Nov. 6, 2007 (MD) .................................. 2007 0302
Mar. 17, 2008 (MD) .................................. 2008 0075

(51) Int. Cl.
A61K 31/155 (2006.01)
A61K 9/00 (2006.01)
A61K 9/02 (2006.01)
A61K 47/44 (2017.01)
A61P 29/02 (2006.01)

(52) U.S. Cl.
CPC .......... *A61K 31/155* (2013.01); *A61K 9/0034* (2013.01); *A61K 9/02* (2013.01); *A61K 47/44* (2013.01); *A61P 29/02* (2018.01)

(58) Field of Classification Search
CPC .... A61K 31/155; A61K 47/44; A61K 9/0034; A61K 9/02; A61P 29/02
See application file for complete search history.

(56) References Cited

U.S. PATENT DOCUMENTS

| 3,934,580 | A | 1/1976 | Cournut |
| 3,993,057 | A | 11/1976 | Ramwell |
| 3,995,636 | A | 12/1976 | Murray et al. |
| 4,016,270 | A | 4/1977 | Pharriss et al. |
| 4,186,742 | A | 2/1980 | Donald |
| 4,241,087 | A | 12/1980 | Mir et al. |
| 4,340,055 | A | 7/1982 | Sneider |
| 4,548,943 | A | 10/1985 | Finizio |
| 4,582,717 | A | 4/1986 | von Bittera et al. |
| 4,615,697 | A | 10/1986 | Robinson |
| 4,728,640 | A | 3/1988 | Labrie et al. |
| 4,743,589 | A | 5/1988 | Labrie et al. |
| 5,026,703 | A | 6/1991 | Bock et al. |
| 5,081,138 | A | 1/1992 | Gillard et al. |
| 5,201,326 | A | 4/1993 | Kubicki et al. |
| 5,225,421 | A | 7/1993 | Gillard et al. |
| 5,417,224 | A | 5/1995 | Petrus et al. |
| 5,543,150 | A | 8/1996 | Bologna et al. |
| 5,545,616 | A | 8/1996 | Woodruff |
| 5,667,492 | A | 9/1997 | Bologna et al. |
| 5,670,509 | A | 9/1997 | Evans et al. |
| 5,912,006 | A | 6/1999 | Bockow et al. |
| 5,962,413 | A | 10/1999 | Garfield et al. |
| 6,160,008 | A | 12/2000 | Mizrakh et al. |
| 6,207,696 | B1 | 3/2001 | Peterson et al. |
| 6,245,357 | B1 | 6/2001 | Edgren et al. |
| 6,419,958 | B2 | 7/2002 | Sherman et al. |
| 6,440,445 | B1 | 8/2002 | Nowak et al. |
| 6,451,780 | B1 | 9/2002 | Chwalsz et al. |
| 6,605,303 | B1 | 8/2003 | Karehill et al. |
| 7,148,208 | B2 | 12/2006 | Barkan et al. |
| 2005/0026836 | A1 | 2/2005 | Dack et al. |
| 2007/0088005 | A1 | 4/2007 | Barkan et al. |
| 2010/0305210 | A1 | 12/2010 | Barkan et al. |

FOREIGN PATENT DOCUMENTS

| CN | 1234737 A | 11/1999 |
| CN | 1464788 A | 12/2003 |
| CN | 1922158 A | 2/2007 |
| SU | 599502 A | 6/1984 |
| WO | 2007/029255 A1 | 3/2007 |
| WO | 2007/108004 A2 | 9/2007 |

OTHER PUBLICATIONS

Dr. Jeffrey Ellis, Guest Experts, 2002 (Year: 2002).*
Gravett et al, J Proteome Res. Jan. 2007; 6(1): 89-96. (Year: 2007).*
Coco et al., Am Fam Physician. Aug. 1, 1999;60(2):489-496. (Year: 1999).*
HK, Examinations. 3rd edition. Boston: Butterworths; 1990, Chapter 173 (Year: 1990).*
Alexander, Fertility and Sterility, Modern Trends, vol. 82, No. 1, Jul. 2004. (Year: 2004).*
Jabbour, Endocrine Reviews, vol. 27, Issue 1, Feb. 1, 2006, pp. 17-46. (Year: 2006).*
Mitchell et al. (Human Reproduction vol. 19, No. 8 pp. 1705-1712, 2004) (Year: 2004).*
Friptu et al., (2004) MD2491F1 & Friptu et al., (2005) MD2850F1.
Dawood (1990) Dysmenorrhea. Clin Obstet Gynecol 33(1): 168-178 abstract.
Duzhak et al., "Pharmacology of some methylisothiuronium analogs", CA 1974, XP002410963, abstract.

(Continued)

*Primary Examiner* — Jean P Cornet
(74) *Attorney, Agent, or Firm* — Allan A. Fanucci

(57) ABSTRACT

The present invention relates to methods for treating uterine hypercontractility disorders. in particular, the present invention relates to methods for treating abnormal uterine bleeding and dysmenorrhea comprising administering to women suffering from such disorders a pharmaceutical composition comprising an S-alkylisothiouronium derivative.

19 Claims, No Drawings

(56) References Cited

OTHER PUBLICATIONS

Friptu et al., MD2491F1, 2004 & Friptu et al., MD2580F1, 2005.
Goodwin, "Are prostaglandins proinflammatory, antiinflammatory, both or neither?", J Rheumatol Suppl., 28:26-29 (Mar. 1991).
Harel, "Dysmenorrhea in Adolescents", Ann. N.Y. Acad. Sci. 1135: 185-195 (2008).
Iacovides et al., "What we know about primary dysmenorrhea today: a critical review", Human Reproduction Update, 21(6): 762-778 (Sep. 2015).
Koninckx et al., "Anti-TNF-α treatment for deep endometriosis-associated pain: a randomized placebo-controlled trial", Human Reproduction, 23(9): 2017-2023 (Jun. 2008).
Lu et al., "Anti-TNF-α treatment for pelvic pain associated with endometriosis", Cochrane Database Syst Rev 3: CD008088, 31 pgs. (Mar. 2013).
Omoigui et al., "The biochemical origin of pain: The origin of all pain is inflammation and the inflammatory response. Part 2 of 3—Inflammatory profile of pain syndromes", Medical Hypotheses 69(6):1169-1178 (Aug. 2007).
International Search Report and Written Opinion, Appl. No. PCT/IL2008/001466, dated Mar. 9, 2009.
Barkan et al., U.S. Appl. No. 12/741,759, Restriction Requirement, dated Sep. 18, 2012.
Barkan et al., U.S. Appl. No. 12/741,759, Non-Final Rejection, dated Oct. 14, 2016.
Barkan et al., U.S. Appl. No. 12/741,759, Final Rejection, dated Aug. 1, 2017.
Barkan et al., U.S. Appl. No. 12/741,759, Advisory Action, dated Oct. 2, 2017.
Barkan et al., U.S. Appl. No. 12/741,759, Non-Final Rejection, dated Feb. 6, 2018.
Barkan et al., U.S. Appl. No. 12/741,759, Final Rejection, dated Nov. 21, 2018.
Barkan et al., U.S. Appl. No. 12/741,759, Advisory Action, dated Feb. 4, 2019.
Barkan et al., U.S. Appl. No. 12/741,759, Non-Final Rejection, dated Jul. 25, 2019.
Barkan et al., U.S. Appl. No. 12/741,759, Final Rejection, dated Mar. 3, 2020.
Barkan et al., U.S. Appl. No. 12/741,759, Advisory Action, dated Jun. 18, 2020.

\* cited by examiner

S-ALKYLISOTHIOURONIUM DERIVATIVES FOR TREATING UTERINE HYPERCONTRACTILITY DISORDERS

CROSS-REFERENCE TO RELATED APPLICATIONS

This application is a continuation-in-part of U.S. application Ser. No. 12/741,759 filed Aug. 16, 2010 which is a 371 of PCT application no. PCT/IL08/01466 filed Nov. 6, 2008, which claims the benefit of Republic of Moldova applications nos. 2007 0302 filed Nov. 6, 2007 and 2008 0075 filed Mar. 17, 2008, the entire content of each of which is expressly incorporated herein by reference thereto.

FIELD OF THE INVENTION

The present invention relates to methods for treating uterine hypercontractility disorders. In particular, the present invention relates to methods for treating abnormal uterine bleeding and dysmenorrhea comprising administering to women suffering from such disorders a pharmaceutical composition comprising an S-alkylisothiouronium derivative.

BACKGROUND OF THE INVENTION

Abnormal Uterine Bleeding

Pathological or abnormal uterine bleeding includes metrorrhagia, menorrhagia, and hypermenorrhea. The average blood loss during normal menstruation is about 30 ml over a period that lasts for an average of 5 days. If the blood loss exceeds 80 ml, it is classified as pathological or abnormal.

Metrorrhagia is defined as bleeding that may or may not be accompanied by pain and that cannot be linked to menstruation or cycle. If it lasts over 7 days, the blood loss often exceeds 80 ml.

Menorrhagia is menstruation that may or may not be accompanied by pain, normally every 27-28 days, which, when it lasts over 7 days, is associated in most cases with an increased blood loss of over 80 ml.

Hypermenorrhea is defined as menstruation that may or may not be accompanied by pain, normally every 27-28 days for 4-5 days with an elevated blood loss of over 80 ml.

Abnormal uterine bleeding is typical of adolescence and of the time of menopause, in which follicle-stimulating disorders, anovulation, and yellow-body and follicle persistence occur in clusters, The incidence of abnormal uterine bleeding is high and represents one of the most frequent reasons for gynecological consultation for women of reproductive age.

Abnormal uterine bleeding is primarily caused by the presence of leiomyomas or fibroids in the uterus. Other causes for abnormal uterine bleeding are endometrial polyps, adenomyosis, perimenopausal hormonal transition, as well as idiopathic bleeding (i.e., bleeding for which there is no obvious cause). Furthermore, abnormal uterine bleeding often results from the use of progestin-only contraceptives.

Current therapies for abnormal uterine bleeding are limited. Surgical therapies include hysterectomies, myomectomies, and endometrial ablation. These therapies require anesthesia and can result in significant morbidity and, rarely, mortality.

Current non-surgical therapies for abnormal uterine bleeding focus on the manipulation of the steroid hormone environment, including use of oral contraceptives, GnRH agonists and antagonists, and progestins. These therapies result in limited efficacy and/or a significant impact on other steroid hormone-dependent tissues, including breast or bone.

Dysmenorrhea

Dysmenorrhea is a common repetitive disorder affecting female adolescents and women, and is closely associated with the menstrual cycle. There are two types of dysmenorrhea that are most prevalent: primary dysmenorrhea and secondary dysmenorrhea. In primary dysmenorrhea there is no underlying or associated organic pathology of the uterus, fallopian tubes, or ovaries. In secondary dysmenorrhea, an organic pathology in the uterus, fallopian tubes, or ovaries does exist. Some causes of secondary dysmenorrhea are endometriosis, uterine myomas, uterine polyps, uterine adhesions, ovarian cysts, adenomyosis, pelvic inflammatory disease (PID), and the presence of an intrauterine device.

While primary and secondary dysmenorrheas require different management or therapy (the latter type usually requiring surgery), both types involve increased levels of prostaglandin synthesis. Hence, the symptomology of dysmenorrhea resembles that of the side effects of prostaglandin administration, namely, nausea, vomiting, diarrhea, vasoconstriction (i.e., uterine ischemia), and severe uterine cramps. Irritability and other psychological disturbances are also symptoms of dysmenorrhea.

The common therapies for primary dysmenorrhea are administration of oral contraceptives (endocrine therapy) and prostaglandin synthetase inhibitors, particularly non-steroidal anti-inflammatory drugs (NSAIDs). However, oral contraceptives are not the primary choice of treatment for all women of child-bearing years as they carry numerous contraindications, and must be taken regularly at least three (sometimes four) weeks of the month.

Prostaglandin synthetase inhibitors (PSIs), on the other hand, are given typically 2-3 days of the menstrual cycle for treating primary dysmenorrhea. Thus, while NSAIDs are predominantly the treatment of choice for primary dysmenorrhea over oral contraceptives, NSAIDs exert side effects, particularly various gastrointestinal disorders (e.g., gastric ulceration), renal dysfunction, and disturbances of the central nervous system (e.g., headache, dizziness, and drowsiness). These side effects are problematic in treating women who desire to become pregnant as NSAIDs have also been shown to reduce female fertility and to increase the risk of spontaneous abortions. It is therefore recommended to avoid the use of NSAIDs when treating women who wish to conceive.

Other drug-related therapies for dysmenorrhea include progesterone-medicated intrauterine devices, and calcium antagonists (to inhibit muscle contraction). Limited efficacy has been observed with administration of betamimetic agents, and tocolytic agents (i.e., ethanol). The management of secondary dysmenorrhea generally entails elucidating the underlying organic pathology and treating it usually with surgery. Any medicinal therapy administered to a woman with secondary dysmenorrhea is an interim measure to bring some relief of symptoms while the underlying pathology is elucidated and/or the patient awaits appropriate surgery. However, there are certain instances of secondary dysmenorrhea where a medicinal management is appropriate. For example, women who develop dysmenorrhea from the use of an IUD are being treated with a prostaglandin synthetase inhibitor.

U.S. Pat. No. 5,962,413 to Garfield et al. discloses methods of regulating the nitric oxide dependent contractility of the uterus of a female mammal comprising administering to a female mammal afflicted with dysmenorrhea, dysfunctional uterine bleeding, preterm labor or postpartum hemorrhage a nitric oxide synthase substrate and/or a nitric oxide donor alone or in combination with one or more of a prostaglandin inhibitor, a prostacyclin-mimetic, a progestin, an oxytocin antagonist or a β-agonist.

U.S. Pat. No. 6,440,445 to Nowak et al. discloses methods for treating abnormal uterine bleeding via application of compounds that block uterine stromal cell response to angiogenic factors, by blocking receptors in the uterine epithelial or stromal cells to growth factors, and/or by inhibiting other receptors to these growth factors. The compounds include interferons, heparin, heparin-like polyaromatic anionic compounds, heparin-sulfated-based compounds, secreted or soluble FGF receptors, and/or RGD peptide.

U.S. Pat. No. 6,4511,780 to Chwalsz et al. discloses methods for the treatment of dysfunctional uterine bleeding comprising administering to a woman in need of said treatment a progesterone antagonist.

U.S. Pat. No. 5,912,006 to Bockow et al. discloses methods for reducing or alleviating the discomforting symptoms associated with menstruation, particularly with menstruation pain. The methods comprise locally or topically administering to a subject in need of such treatment a composition comprising an omega fatty acid and a cyclo-oxygenase inhibitor.

U.S. Pat. No. 6,207,696 to Peterson et al. discloses methods and compositions for preventing or treating conditions or disorders of the female reproductive system comprising administering histidine alone or in combination with other therapeutic agents.

U.S. Pat. No. 7,148,208 to Barkan et al. discloses methods for treating headaches and migraines as well as nausea and vomiting comprising administering to a subject in need of such treatments a composition comprising an S-alkylisothiouronium derivative.

International Application Publication No. WO 2007/029255 to some of the inventors of the present invention discloses methods for preventing hypotension and stabilizing blood pressure in hemodialysis patients comprising administering to these patients a pharmaceutical composition comprising an S-alkylisothiouronium derivative.

International Application Publication No. WO 2007/108004 to the inventors of the present invention discloses methods for treating inflammation comprising administering to a subject in need of such treatment a pharmaceutical composition comprising an S-alkylisothiouronium derivative.

Recently in unpublished studies S-ethylisothiouronium bromide has been used to treat abnormal uterine hemorrhages and pelvic pains associated with uterine myoma in women. Although S-ethylisothiouronium bromide was found to be effective in reducing the abnormal uterine hemorrhages and pelvic pains, it exerted short-duration effect accompanied with side effects such as digestive disturbances and complications.

There is still a need for improved methods for treating abnormal uterine bleeding and dysmenorrhea in female subjects having fewer or no side effects or contraindications as compared to the medications currently used for these disorders.

SUMMARY OF THE INVENTION

The present invention provides methods for treating uterine hypercontractility disorders comprising administering to a female subject a pharmaceutical composition comprising an S-alkylisothiouronium derivative.

It is now disclosed that administration of a pharmaceutical composition comprising S-ethylisothiouronium diethylphosphate as the active agent to women suffering from abnormal uterine bleeding reduced and even abrogated the abnormal uterine bleeding.

Surprisingly, it is further disclosed that administration of S-ethylisothiouronium diethylphosphate to women suffering from abnormal uterine bleeding resulted in a long-lasting effect as a few months after cessation of the treatment, the menstrual cycles in these women showed normal duration and interval.

It is further disclosed that administration of a pharmaceutical composition comprising S-ethylisothiouronium diethylphosphate to women suffering from primary or secondary dysmenorrhea decreased and even eradicated uterine cramping and/or contractions due to dysmenorrhea as well as the intensity and frequency of pelvic pains in these women.

The present invention further discloses that vaginal suppositories containing S-ethylisothiouronium diethylphosphate as the active agent are highly advantageous means for treating abnormal uterine bleeding and dysmenorrhea due to their high therapeutic efficiency having little or no side effects, cost effectiveness and good local tolerability.

Unexpectedly, S-ethylisothiouronium diethylphosphate was found to be preferable over S-ethylisothiouronium bromide as it exerted longer bioactivity, higher efficacy, and little or no side-effects.

According to a first aspect, the present invention provides a method for treating a uterine hypercontractility disorder in a woman comprising administering to the woman a therapeutically effective amount of a pharmaceutical composition comprising as an active agent a compound of formula I:

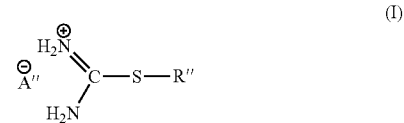

wherein
R″ is a straight or branched alkyl, optionally substituted by halogen; and
A″(−) is an anion derived from a phosphorous containing acid, a phosphorous acid ester and. a phosphorous acid amide.

According to some embodiments, the anion of the compound of formula I is derived from a mono or di-alkyl ester of a phosphate or phosphite.

According to additional embodiments, the compound is selected from the group consisting of:
S-methylisothiouronium methylphosphite;
S-methylisothiouronium dimethylphosphate;
S-ethylisothiouronium metaphosphate;
S-ethylisothiouronium ethylphosphite;
S-ethylisothiouronium diethylphosphate;
S-propylisothiouronium propylphosphite;
S-isopropylisothiouronium metaphosphate;
S-isopropylisothiouronium isopropylphosphite;
S-butylisothiouronium dibutylphosphate; and
S-isobutylisothiouronium isobutylphosphite.

According to a certain embodiment, a preferred compound is S-ethylisothiouronium diethylphosphate.

According to some embodiments, the uterine hypercontractility disorder is selected from the group consisting of abnormal uterine bleeding, dysmenorrhea, and preterm labor. According to certain embodiments, the uterine hypercontractility disorder is abnormal uterine bleeding or dysmenorrhea. According to yet further embodiments, the abnormal uterine bleeding is selected from the group consisting of metrorrhagia, menorrhagia, and hypermenorrhea. According to a certain embodiment, the abnormal uterine bleeding is due to uterine fibrinoids or myomas. According to still further embodiments, dysmenorrhea is selected from the group consisting of primary dysmenorrhea and secondary dysmenorrhea. According to a certain embodiment, dysmenorrhea is primary dysmenorrhea.

According to further embodiments, the pharmaceutical composition is formulated in a form selected from the group consisting of a solution, suspension, emulsion, tablet, capsule, powder, vaginal or rectal suppository, intravaginal tampon, intravaginal ring, intravaginal pessary, intravaginal sponge, medicated intrauterine device (IUD), spray, cream, gel, ointment, and a sustained-release formulation. According to an exemplary embodiment, the pharmaceutical composition is formulated as a vaginal suppository.

According to yet further embodiments, administration of the pharmaceutical composition is performed by oral, intravenous, intramuscular, intraperitoneal, intranasal, intravaginal, cervical, intrauterine, rectal, transmucosal or transdermal administration route. According to a certain embodiment, administration of the pharmaceutical composition is performed by oral administration route. According to an exemplary embodiment, administration of the pharmaceutical composition is performed by vaginal administration route.

According to further embodiments, the pharmaceutical composition is administered prior to onset of the uterine contractility disorder, during the uterine contractility disorder, or both. According to still further embodiments, the pharmaceutical composition is administered prior to menses, during menses, or both. According to an exemplary embodiment, the pharmaceutical composition is administered once a day during menses to alleviate dysmenorrhea. According to another exemplary embodiment, the pharmaceutical composition is administered once a day during abnormal uterine bleeding. Typically, the pharmaceutical composition is administered once a day for 1 day to 10 days, preferably once a day for 1 day to 8 days, more preferably once a day for 1 day to 6 days, or up to the disappearance of the uterine hypercontractility disorder or the manifestations associated therewith, particularly of abnormal uterine bleeding. It is to be appreciated that the present invention encompasses administration of the pharmaceutical composition 2, 3, 4, or more times a day, so long as the hypercontractility disorder is treated or alleviated. Similarly, the present invention encompasses administration of the pharmaceutical composition once in two days, once in three days, and the like, as long as the hypercontractility disorder is treated or alleviated.

According to some embodiments, if the pharmaceutical composition is formulated as a vaginal suppository, the therapeutically effective amount of the compound of formula I range from about 1 mg to about 400 mg, alternatively from about 50 mg to about 200 mg. According to a certain embodiment, the therapeutically effective amount of S-ethylisothiouronium diethyiphosphate in a vaginal suppository is of about 100 mg per unit dose.

According to another aspect, the present invention provides a vaginal or cervical device comprising a therapeutically effective amount of a pharmaceutical composition comprising as an active agent a compound of formula I:

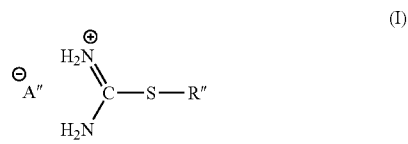

wherein
R" is a straight or branched alkyl, optionally substituted by halogen; and
A" (−) is an anion derived from a phosphorous containing acid, a phosphorous acid ester and. a phosphorous acid amide.

According to some embodiments, the anion of the compound of formula I present in the pharmaceutical composition of the vaginal or cervical device is derived from a mono or di-alkyl ester of a phosphate or phosphite.

According to additional embodiments, the compound present in the pharmaceutical composition of the vaginal or cervical device is selected from the group consisting of:
S-methylisothiouronium methylphosphite;
S-methylisothiouronium dimethylphosphate;
S-ethylisothiouronium metaphosphate;
S-ethylisothiouronium ethylphosphite;
S-ethylisothiouronium diethylphosphate;
S-propylisothiouronium propylphosphite;
S-isopropylisothiouronium metaphosphate;
S-isopropylisothiouronium isopropylphosphite;
S-butylisothiouronium dibutylphosphate; and.
S-isobutylisothiouronium isobutylphosphite.

According to a certain embodiment, a preferred compound is S-ethylisothiouronium diethylphosphate.

According to some embodiments, the vaginal or cervical device is selected from the group consisting of a medicated intravaginal tampon, intravaginal ring, intravaginal pessary, intravaginal sponge, and medicated intrauterine devices (IUDs), According to another aspect, the present invention provides a vaginal suppository comprising a therapeutically effective amount of S-ethylisothiouronium diethylphosphate. According to a certain embodiment, the therapeutically effective amount of S-ethylisothiouronium diethylphosphate in the vaginal suppository ranges from about 1 mg to about 400 mg, alternatively from about 2 mg to about 200 mg, or alternatively 100 mg.

According to another aspect, the present invention provides use of a compound of formula

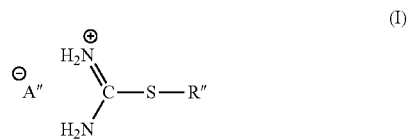

wherein
R" is a straight or branched alkyl, optionally substituted by halogen; and
A" (−) is an anion derived from a phosphorous containing acid, a phosphorous acid ester and a phosphorous acid amide, for the manufacturing of a medicament for treating a uterine hypercontractility disorder.

According to a further aspect, the present invention provides a pharmaceutical composition comprising as an active agent a compound of formula I:

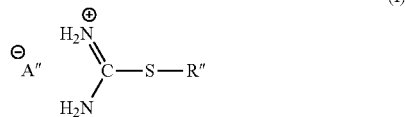

wherein
R" is a straight or branched alkyl, optionally substituted by halogen; and
A" (−) is an anion derived from a phosphorous containing acid, a phosphorous acid ester and a phosphorous acid amide, for treating a uterine hypercontractility disorder.

These and other embodiments of the present invention will be better understood in relation to the description, examples and claims that follow.

DETAILED DESCRIPTION OF THE INVENTION

The present invention provides effective and highly safe methods for treating or preventing uterine hypercontractility disorders in female subjects. The methods comprise administering to a subject suffering from a uterine hypercontractility disorder a pharmaceutical composition comprising as an active agent an S-alkylisothiouronium derivative, The present invention further provides devices for treating or preventing uterine hypercontractility disorders in female subjects, the devices comprise an S-alkylisothiouronium derivative as the therapeutically active agent.

Uterine hypercontractility disorders that include abnormal uterine bleeding, dysmenorrhea, and preterm labor are significant health problems. Abnormal uterine bleeding is a common clinical problem in gynecology that affects women in reproductive years and in menopause. Dysmenorrhea, painful uterine contractions or cramping, primarily during the menstrual period, affects almost all gonadal women. Similarly, preterm labor occurs in a significant proportion (about 10%) of pregnant women and is the leading cause of fetal mortality and morbidity.

As noted above, the current medications for reducing or eliminating uterine contractions or cramping due to dysmenorrhea are NSAIDs or oral contraceptives. While NSAIDs are the first line of therapy for dysmenorrhea, these drugs exert several side effects, the most common and prominent of which is gastric ulceration. NSAIDs have also been shown to affect the reorganization of the three-layer structure of the uterus and hence to reduce impregnation, to reduce ovulation, and to increase the risk of spontaneous abortions, thus impairing women fertility. Contraceptives, the second line of therapy of dysmenorrhea, have various contraindications, including coronary artery disease, deep vein thrombosis, and pulmonary embolism. As NDAIDs and contraceptives reduce, significantly impair, or even prevent women fertility, women who wish to conceive should avoid these two types of medications.

The present invention fulfills the need for methods of reducing or eliminating uterine contractions or cramping due to dysmenorrhea which are essentially devoid of side effects or contraindications. The methods of the present invention are particularly useful for fertile women who suffer from uterine contractions or cramping due to dysmenorrhea and who wish to get pregnant as these methods do not impair women fertility.

It is now shown that intravaginal administration of S-ethylisothiouronium diethylphosphate abrogated uterine cramps in about 95% of the treated women who suffered from primary dysmenorrhea. This effect was found to be greater than that achieved by NSAIDs which relieve uterine cramps in about 85% of women suffering from primary dysmenorrhea (Iacovides et al. Hum. Reprod Update 21(6): 772-778, 2015). Thus, the methods of the present invention are highly advantageous as these methods are more efficacious than NSAIDs to eliminate both uterine contractions and pelvic pain due to dysmenorrhea with fewer or no detectable side effects.

The present invention further discloses that intravaginal administration of S-ethylisothiouronium diethylphosphate to women not only reduced or eliminated uterine cramps, but also reduced or eliminated pelvic pain due to dysmenorrhea. Thus, the methods of the present invention eliminated uterine contractions due to dysmenorrhea and actually removed the underlying cause of the pelvic pain. The methods of the present invention therefore avoid the need to treat pelvic pain due to dysmenorrhea. It is to be noted that various anti-pyretic or analgesic agents, such as acetaminophen or dipyrone, or opiates such as morphine, can reduce or eliminate pelvic pain, but cannot eliminate uterine contractions in women suffering from dysmenorrhea, and therefore these women suffer from increased uterine bleeding. Also, β₂ adrenoreceptor agonists used to treat premature labor by relaxing uterine smooth muscle have been used in the treatment of women with primary dysmenorrhea. However, the effects of β₂ adrenoreceptor agonists on relieving pelvic pain are unclear and have been accompanied with unacceptable side effects, among which dizziness, quivering, tremor, and palpitations have been reported. Thus, the capability of S-ethylisothiouronium diethylphosphate to eliminate both uterine contractions and pelvic pain due to dysmenorrhea with essentially undetectable side effects is highly unexpected.

The methods of the present invention therefore provide advantageous therapy of uterine cramps or contractions due to dysmenorrhea which overcome the drawbacks of the current medications. These unexpected results are a significant improvement over the previously mentioned conventional therapies and represent a recommended and preferred treatment for eliminating uterine contractions due to dysmenorrhea without detectable side effects in any woman in need of such treatment and in particular in women in need of such treatment who also wish to become pregnant.

COMPOUNDS OF THE INVENTION

According to the present invention, S-alkylisothiouronium derivative is a compound of formula I:

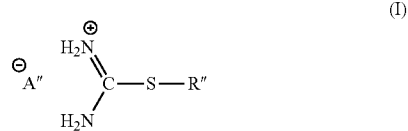

wherein

R" is a straight or branched alkyl, optionally substituted by halogen; and

A" (−) is an anion derived from a phosphorous containing acid, a phosphorous acid ester and a phosphorous acid amide.

According to some embodiments, the anion is derived from a mono or di-alkyl ester of a phosphate or phosphite.

According to additional embodiments the compound is selected from the group consisting of:

S-methylisothiouronium methylphosphite;
S-methylisothiouronium dimethylphosphate;
S-ethylisothiouronium metaphosphate;
S-ethylisothiouronium ethyiphosphite;
S-ethylisothiouronium diethylphosphate;
S-propylisothiouronium propylphosphite;
S-isopropylisothiouronium metaphosphate;
S-isopropylisothiouronium isopropylphosphite;
S-butylisothiouronium dibutylphosphate; and
S-isobutylisothiouronium isobutylphosphite.

According to a certain embodiment, the compound is S-ethylisothiouronium diethylphosphate.

Pharmaceutical Compositions

The pharmaceutical compositions of the present invention comprise an S-alkylisothiouronium derivative and a pharmaceutically acceptable carrier.

The term "pharmaceutically acceptable" means approved by a regulatory agency of the Federal or a state government or listed in the U. S. Pharmacopeia or other generally recognized pharmacopeia for use in animals, and more particularly in humans. The term "carrier" refers to a diluent, adjuvant, excipient, or vehicle with which the therapeutic compound is administered. Such pharmaceutical carriers can be sterile liquids, such as water and oils, including those of petroleum, animal, vegetable or synthetic origin, such as peanut oil, soybean oil, mineral oil, sesame oil and the like, polyethylene glycols, glycerin, propylene glycol or other synthetic solvents. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, propylene glycol, water, ethanol and the like. The composition, if desired, can also contain minor amounts of wetting or emulsifying agents, or pH buffering agents such as acetates, citrates or phosphates. Antibacterial agents such as benzyl alcohol or methyl parabens; antioxidants such as ascorbic acid or sodium bisulfite; chelating agents such as ethylenediaminetetraacetic acid; and agents for the adjustment of tonicity such as sodium chloride or dextrose are also envisioned.

The compositions can take the form of solutions, suspensions, emulsion, tablets, capsules, powders, suppositories, implants, sustained-release formulations and the like depending on the route of administration chosen.

Routes of administration that are appropriate in the practice of the present invention include oral, intramuscular, intraperitoneal, intranasal, intravenous, intravaginal, intrauterine, rectal, transmucosal and transdermal, For oral administration, the pharmaceutical composition of the invention can be formulated as tablets, dragees, capsules, liquids, gels, syrups, slurries, suspensions, and the like. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate. Examples of suitable pharmaceutical carriers are described in "Remington's Pharmaceutical Sciences" by E. W. Martin. Such compositions will contain a therapeutically effective amount of an S-alkylisothiouronium derivative together with a suitable amount of a carrier so as to provide the form for proper administration to the subject.

For parenteral administration, the pharmaceutical composition of the invention can be formulated in aqueous solutions, preferably in physiologically compatible buffers such as Hank's solution, Ringer's solution, or physiological saline buffer. Additionally, suspensions of the active compounds may be prepared as appropriate oily injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents, which increase the solubility of the compounds, to allow for the preparation of highly concentrated solutions. Parenteral formulations may optionally contain one or more additional ingredients among which may be mentioned preservatives (when the formulations are presented in multi-dose containers), buffers to provide a suitable pH value for the formulation, and sodium chloride, or glycerin, to render a formulation isotonic with the blood.

For buccal administration, the compositions may take the form of tablets or lozenges formulated in conventional manner.

The pharmaceutical compositions of the present invention can be formulated in an extended release pharmaceutical dosage form as known in the art (see, for example, U.S. Pat. Nos. 6,605,303; 6,419,958; 6,245,357, the content of which is incorporated by reference as if fully set forth herein).

Thus, an extended release pharmaceutical dosage form of the S-alkylisothiouronium derivatives of the present invention comprise an S-alkylisothiouronium derivative, a polymer, and optionally one or more additional pharmaceutically acceptable excipient or carrier.

Polymers that can be used for the preparation of the extended release pharmaceutical dosage fonn of the present invention include hydrophilic polymers, hydrophobic polymers, and a combination thereof.

Suitable hydrophilic polymers are for instance hydroxypropyl methylcellulose, hydroxypropyl cellulose, ethylhydroxy ethylcellulose, hydroxyethyl cellulose, carboxymethyl cellulose, sodium carboxymethyl cellulose, methyl cellulose, polyethylene oxides, polyvinyl alcohols, tragacanth, and xanthan. These polymers can be used alone or in mixtures with each other.

Hydrophobic polymers are exemplified by for instance polyvinyl chloride, ethyl cellulose, polyvinyl acetate and acrylic acid copolymers, such as Eudragith™. The polymers can be used alone or as mixtures. Alternatively or additionally, hydrophobizing agents can be used for the hydrophobic matrix such as for instance cetanol, cetostearyl alcohol, cetyl palmitate, waxes lice carnauba wax, paraffin, magnesium stearate, sodium stearyl fumarate, and medium- or long-chain glycerol esters alone or in any mixtures.

The extended release pharmaceutical dosage forms of the invention can further comprises binders such as for instance sugars, polyvinyl pyrrolidine, starches and gelatin; surfactants such as non-ionic surfactants such as for instance polysorbate 80, or ionic surfactants such as for instance sodium lauryl sulfate; lubricants such as for instance magnesium stearate, sodium stearyl fumarate, or cetyl palmitate; fillers such as for instance sodium aluminum silicate, lactose, or calcium phosphate; glidants such as for instance talc and aerosol; and antioxidants.

For buccal administration, the compositions may take the form of tablets or lozenges formulated in conventional manner.

For administration by inhalation, the compounds for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

Transmucosal or transdermal administration can be accomplished using preparations in the form of ointments, emulsions, gels, lotions, solutions (e.g., douches), creams or patches (in the case of transdermal delivery). Suitable pharmaceutical carriers for transmucosal or transdermal administration include, for example, polyethylene glycol, propylene glycol, glycerin, isopropanol, ethanol, oleic acid, N-methylpyrrolidone, sesame oil, olive oil, wood alcohol ointments, vaseline, and paraffin, or mixtures thereof.

For transmucosal delivery of a gel, cream, or ointment formulation to the vaginal mucosa, bioadhesive polymer-based carrier compositions are particularly useful. Suitable bioadhesive polymers are, e.g., those that are described in U.S. Pat. No. 4,615,697, the content of which is incorporated herein by reference. Particularly useful polymers are cross-linked polycarboxylic acid polymers having a sufficiently high degree of cross-linking to impart the desired level of bioadhesion to the target epithelial surface. Representative bioadhesive polymer formulations are described, for example, in U.S. Pat. No. 5,543,150 and U.S. Pat. No. 5,667,492. Other additives suitable for incorporation into a bioadhesive polymer formulation include one or more of a preservative, a humectant, a lubricating agent and/or moisturizing agent, a stabilizer, a pigment, a pH modifier (e.g., a base) and purified water. Depending on the formulation additives and the resulting viscosity, such formulations may be administered vaginally as a douche, with a plunger, or as a suppository.

Vaginal suppositories comprising an S-alkylisothiouronium derivative afford constant release over an extended period of time and are particularly useful in treating or preventing abnormal uterine bleeding and dysmenorrhea. Rectal suppositories may also be used to deliver an S-alkylisothiouronium derivative. Typical base carriers for vaginal or rectal suppositories include, for example, natural, synthetic or partially synthetic fats, waxes and derivative thereof from animal, vegetable, or mineral origin. Specific examples include olive oil, corn oil, castor oil, hydrogenated oils, petrolatum, solid paraffin, liquid paraffin, carnuba wax, bees wax, lanolin, partially or totally synthetic esters of glycerol fatty acid, mono, di, or triglycerides of saturated or unsaturated fatty acids, and well-known carriers in the art. Other additives suitable for incorporation into a suppository of the invention include preservatives, stabilizers, surfactants, pigments, pH modifiers and purified water as known in the art.

Medicated devices suitable for vaginal or cervical implant include tampons, vaginal rings, vaginal cups, cervical cups, vaginal pessaries, vaginal sponges, and intrauterine devices (IUDs). A tampon may be impregnated and/or coated with efficacious amount of slow-release S-alkylisothiouronium derivative for a period of time consonant with safe and hygienic tampon usage (typically one tampon every 4 to 8 hours). Examples of tampons impregnated or coated with sustained-release therapeutic agents are found, e.g., in U.S. Pat. Nos. 3,995,636, 4,186,742, 4,3.40,055, 4,582,717, 5,201,326, and 5,417,224; the content of which is incorporated herein by reference. S-alkylisothiouronium derivative can be incorporated/impregnated into an over-wrap sheet of non-woven material which is permeable by body fluids and which is superimposed on a first sheet of absorbent material which forms the corpus of the tampon when the sheets are rolled or formed into the desired tampon shape, with the S-alkylisothiouronium derivative-containing layer remaining on the outermost surface. Alternatively, the S-alkylisothiouronium derivative can be deposited between the corpus absorbent sheet and the permeable over-wrap sheet during manufacturing. Alternatively, S-alkylisothiouronium derivative can be incorporated into a tampon cover made from a hardened collagen or gelatin foam with a release retardant material such as triglycerides of higher fatty acids melting at body temperature, for application to an absorbent natural or synthetic tampon core.

Another mode of manufacturing an S-alkylisothiouronium derivative-impregnated tampon incorporates the S-alkylisothiouronium derivative into a suppository base formulation which is melted, syringe-impregnated into tampons, and allowed to cool. Alternatively, pre-formed tampons can he coated with the melted suppository formulation containing the active agent. either case, the result is a tampon that releases S-alkylisothiouronium derivative gradually as the suppository base melts in the presence of body temperature. Useful suppository auxiliaries are those recited hereinbefore as well as those described in U.S. Pat. No. 4,582,717.

In vaginal and cervical devices such as vaginal rings, vaginal cups, cervical cups, vaginal pessaries, vaginal sponges, the compound is incorporated into these devices as a cream, lotion, foam, solution, paste, ointment, or gel.

Medicated IUDs include noncontraceptive as well as contraceptive IUDs, non-bio-erodible, partially bio-erodible, and completely bio-erodible IUDs. Examples of active agent-releasing intrauterine devices that could be used in the practice of the present invention are described in U.S. Pat. Nos. 3,934,580, 3,993,057, and 4,016,270, incorporated herein by reference. Typically, the IUD is made of a flexible polymeric non-eroding core and is over-coated with a bio-erodible coat material containing an S-alkylisothiouronium derivative. Alternatively, the IUD core can be a bio-erodible material containing the S-alkylisothiouronium derivative for sustained-release, and may or may not further comprise an active agent-releasing outer coat. The tatter construction makes it unnecessary to remove the device after the entire medicament is released. For example, an active intrauterine device within the practice of the invention can consist of a non-bioerodible hydrophobic substrate of high mechanical resiliency, Wherein the substrate comprises, within the volume thereof, inclusions of polymerized hydrophilic substances, grafted on the hydrophobic substrate and cross-linked, in which an S-alkylisothiouronium derivative has been stored and which will perfuse through the hydrophobic substrate when the latter is placed in an aqueous medium. Materials suitable for the hydrophobic substrate are polymerized thermoplastic products such as, e.g., vinyl acetate, polyethylene or a co-polymer of vinyl acetate and polyethylene, or, more generally, an ethylene co-polymer, a polyether, a polyurethane or a polyacrylonitrile. Materials suitable for the hydrophilic substances include ethylene-glycol acrylate, ethylene-glycol methacrylate, acrylamide, methacrylamide, acrylamide methylol, acrylamide diacetone or an unsaturated acidic product such as malic acid, acrylic acid, methacrylic acid, fumaric acid, itaconic acid or propylene glycol acrylate or methacrylate. Also, polypropylene, polyamides, polyesters such as ethylen-glycol, polyterephtalate, polyvinyl chloride, polyformaidehyde chloride, polycarhonates and olytetrafluoroethylene ("Teflon") may be used. In addition to storing therapeutic amounts of the S-alkylisothiouronium derivative in the hydrophilic inclusions, contraceptive agents such as copper-, zinc-, cobalt-, lead- and cadmium-salts, synthetic sexual steroids (such as derivatives of testosterone, the derivatives of nortestosterone, norethisterone, norethisterone acetate, norethynodrel, ethynodiol diacetate, norgestrienone, norgestrel, chlormadynone acetate, medroxyprogesterone acetate, megestrol acetate, anagestrone acetate and prostaglandin) and ovulation inhibiting estrogens (such as ethynol estradiol and mestranol) can be stored as well.

For an intrauterine device that is at least partially bioerodible, the materials must be non-toxic and non-irritating to the endometrium of the uterus, and the bioerosion end products of which must also be non-toxic and easily eliminated from the body. Exemplary bioerodible materials include both natural and synthetic materials such as (a) structural proteins and hydrocolloids of animal origin; (b) polysaccharides and other hydrocolloids of plant origin; and (c) synthetic polymers. Some of these matrix materials are suitable as in their native form but others, particularly hydrocolloids, require insolubilization either by chemical modification, or physical modification, such as orientation, radiation cross-linking, etc, Exemplary of the first category are: native and modified collagens, muscle proteins, elastin, keratin, resilin, fibrin, etc. Exemplary of polysaccharides and plant hydrocolloids are: a ligin, pectin, carrageenan, heparin, chondroitin sulfate, Agar-agar, Guar, locust bean gum, gum arabic, gum Karaya, tragacanth, gum Ghatti, starch, oxystarch, starch phosphate, carboxymethyl starch, sulfaethyl starch, aminoethyl starch, amido ethyl starch, starch esters such as starch maleate, succinate, benzoate and acetate, and mixtures of starch and gelatin; cellulose and its derivatives such as modified cellulose, such as partially hydroxyethylated cotton obtained by the treatment of cotton with ethylene oxide or partially carboxymethylated cotton obtained by the treatment of cotton with caustic and choroacetic acid. Examples of synthetic polymers are: polyvinyl alcohol), polyethylene oxide), poly(acrylamide), poly(vinyl pyrrolidone), poly(ethyleneimine), poly(vinyl imidazole), poly(phosphate), synthetic polypeptides, polyvinyl alkyl ether, polyacryl-and polymethacrylamides, and copolymers of acrylamide and methacrylamide with up to 40% by weight of N-methylene bisacrylamide or N,N-dimethylol urea; polyalkyl aldehydes, water soluble hydrophilic polymers of uncross-linked hydroxyalkyl acrylates and methacrylates, polyalkylene carbonates, and the like. Any bioerodible material which is compatible with 5-alkylisothiouronium derivative and non-toxic and which has the desired erosion and release rates can be used. Typically cross-linking agents (e.g., aldehydes, such as acetaldehyde, thrmaldehyde, acrolein, crotonaldehyde, glutaraldehyde, glyoxal, dimethylol urea, trimethylol melamine; tetra(methoxymethyl)urea, melamine, epichlorohydrin, and hexamethylene tetramine) and plasticizers (e.g., acetyl tri-n-butyl citrate, epoxidized soy bean oil, glycerol monoacetate, polyethylene glycol, propylene glycol dilaurate, decanol, dodecanol, 2-ethyl hexanol, 2,2-butoxy-ethoxyethanol and the like) are added to impart the desired rate of bioerosion and flexibility, respectively, to the IUD. Intrauterine devices include, for example, pessaries, spirals or coils, such as the Mirena® coil.

Uses of S-Alkylisothiouronium Derivatives

The present invention provides effective and highly safe methods for treatment of uterine hypercontractility disorders in female subjects. The methods comprise administering to a subject suffering from a uterine hypercontractility disorder a pharmaceutical composition comprising as an active agent an S-alkylisothiouronium derivative.

By "treatment" is meant the ability to effectively abate a uterine hypercontractility disorder or the manifestations associated therewith once they have begun. It is to be appreciated that the term treatment includes prophylaxis. By "prophylaxis" is meant the ability to prevent the onset of a uterine hypercontractility disorder or the manifestations associated therewith.

The term "uterine hypercontractility disorder" refers to abnormal or dysfunctional uterine bleeding, dysmenorrhea, and preterm labor.

The term "abnormal uterine bleeding" or "dysfunctional uterine bleeding" which are used interchangeably throughout the specification and claims include excessive uterine bleeding in frequency and/or volume, whether it is within or outside a normal cycle, in the absence of cycling, or in association with abnormal cycling, Thus, abnormal uterine bleeding includes metrorrhagia, menorrhagia, and hypermenorrhea.

The most common cause of abnormal uterine bleeding is the presence of leiomyomas (fibroids) in the uterus. Other causes of abnormal uterine bleeding include adenomyosis, endometrial polyps, progestin only contraceptives, premenopause, pregnancy, postpartum, anovulation, and idiopathic abnormal uterine bleeding with no obvious cause.

The major manifestation of abnormal or dysfunctional uterine bleeding is anemia. The major manifestations of dysmenorrhea are nausea, vomiting, diarrhea, vasoconstriction, i.e., uterine ischemia, which leads to severe uterine cramping. Irritability and other psychological disturbances are also manifestations of dysmenorrhea. Cramps associated with pre-menstruation and/or menses are a symptom of primary dysmenorrhea and can be prevented or treated by preferably commencing administration of an S-alkylisothiourea derivative to the woman either prior to onset of menstruation or, alternatively, on first occurrence of menstrual cramps, with continued administration for as many days of menses that the menstrual cramps persist.

The secondary dysmenorrheas that can be treated with an S-alkylisothiouronium derivative have an underlying pathologic origin, such as endometriosis, pelvic inflammation, pelvic infection, adenomyosis, uterine myoma, uterine polyps, uterine adhesions, congenital malformations of the Mullerian system, cervical stenosis, ovarian cysts, pelvic congestion syndrome, polycystic ovary syndrome(PCOS), and Allen-Master's syndrome.

Thus, according to the present invention, an S-alkylisothiouronium derivative of the present invention can reduce the severity and/or duration and/or frequency of abnormal uterine bleeding. An S-alkylisothiouronium derivative of the present invention can also reduce the severity and/or duration and/or frequency of pelvic pains associated with primary or secondary dysmenorrheas due to its ability to reduce or eliminate uterine cramping. Preferably, an S-alkylisothiouronium derivative of the invention can prevent the onset or occurrence of abnormal uterine bleeding and/or pelvic pains, the latter associated with primary or secondary dysmenorrheas and caused by uterine cramping.

Routes of administration that are appropriate in the practice of the present invention include oral, intravenous, intramuscular, intraperitoneal, intranasal, intravaginal, intrauterine, rectal, transmucosal and transdermal administration routes.

Administration of therapeutic doses of an S-alkylisothiouronium derivative with other therapeutically active agents useful in treating or alleviating uterine hypercontractility disorders, particularly abnormal uterine bleeding and dysmenorrheal, is also encompassed in the present invention. In methods of co-administering an S-alkylisothiouronium derivative with one or more additional therapeutically active agents, it is envisioned that all of the active agents can be administered either simultaneously or sequentially. Accordingly, the effective dose of an S-alkylisothiouronium can be co-formulated with the additional active agent(s) in a single composition. Alternatively, where sequential co-administration is more appropriate or practical, then separate dosage forms for administration by the same or different routeof administration, will be used.

Compounds suitable for "another therapeutically active agent" are those agents which are useful for abating or treating disorders such as dysmenorrhea and pre-term labor, agents for treating endornetrial pain, and agents for treating underlying reproductive disorders which as a result of correction or abatement cause dysmenorrhea. Examples of therapeutic agents for treating dysmenorrhea include, hut are not limited to, tocolytic oxytocin antagonists (e.g., $\beta_2$-adrenergic agonists (ritodrine, terbutalin, and albuterol), magnesium sulfate, ethanol, amide substituted spiroindanylcamphorsulfonyl oxytocin antagonists, peptide oxytocin antagonists (e.g., as disclosed in U.S. Pat. No. 5,026,703) and Spiro cyclic compounds such as Spiro indene-piperidine disclosed e.g., in U.S. Pat. No. 5,670,509); nonsteroidal antiinflammatory drugs/prostaglandin synthetase inhibitors (e.g., aspirin, diflunisal, ibuprofen, indomethacin, clinoril, tolectin, zomepirac, naproxen, ketoprofen, suprofen, meclofenamate, meclofenamic acid, flufenamic acid, mefenamic acid, ketorolac, cataflam, diclofenac, sodium, phenylbutazone, p-chloromercuribenzoate and piroxicam); calcium supplements, pharmaceutically acceptable salts of calcium, and other pharmaceutically-recognized administrable forms of calcium; a heteropolycyclo-substituted heterocyclic amide thromboxane $A_2$ receptor antagonist (e.g., ifetroban or a pharmaceutically acceptable salt thereof); certain amidinoureas (e.g., those disclosed in U.S. Pat. No. 4,241,087), antiinflammatory arylmethylene and arylmethylindenoimidazoles (e.g., disclosed in U.S. Pat. No. 4,548, 943); and therapeutic peptides (e.g., U.S. Pat. No. 4,728, 640). Representative therapeutic agents for treating endometriosis include hormones, especially contraceptive regimens, danazol, and long-acting gonadotropin-releasing hormone analogues; therapeutic peptides (e.g., those disclosed in U.S. Pat. No. 4,728,640 and U.S. Pat. No. 4,743, 589); and nonsteroidal antiinflammatory drugs, such as those recited previously. Representative therapeutic agents for managing pre-term or premature labor include certain NSAIDs (e.g., clinoril (Sulindac)), an activin antagonist (e.g., human follistatin, a polyclonal or monoclonal antibody or immunogenic fragment thereof capable of binding to activin, e.g., as described in U.S. Pat. No. 5,545,616); smooth muscle relaxant S-nitrosothiols; certain aromatase inhibitors (e.g., 4-hydroxy-4-androstene-3,17-dione or 4-acetoxy-4-androstene-3,17-dione); inhibitors of leukotriene biosynthesis, e.g., aryl, hetero, poly substituted indoles (e.g., as disclosed in U.S. Pat. No. 5,081,138 and U.S. Pat. No. 5,225,421); quinolin-2-ylmethoxy indoles, fluoro-substituted quinoline indoles, quinolin-2-ylmethoxy tetrahydrocarbazoles, tetrahydrocarbazole alkanoic acids, quinoline ether a alkanoic acids, cycloalkyl (e.g., heptyl) indole alkanoic acids, indenyl hydroxamic acids, and hydroxy ureas. Many of these pre-term labor therapeutics (e.g., the tocolytic oxytocin receptor antagonists, the heteropolycyclo indoles, the quinolyl indoles, the tetrahydrocarbazole alkanoic acids and the cycloalkyl indole alkanoic acids to name a few) are also useful for treating dysmenorrhea. Representative therapeutic agents for treating ovary dysfunction include hormone therapeutics and D-chiroinositol. The above listings are intended to be representative, and not limiting, of the types of additional therapeutic agents that can advantageously be co-administered with a therapeutic amount of a compound of formula I. Other agents for treating female reproductive conditions or disorders and which are readily appreciated by the treating physician or veterinarian are also intended in the present embodiment.

Pharmaceutical compositions suitable for use in context of the present invention include a therapeutically effective amount of the active agents to achieve the intended purpose. More specifically, "a therapeutically effective amount" means an amount of a compound effective to prevent, alleviate or treat a uterine disorder, particularly abnormal uterine bleeding and dysmenorrhea, in the subject being treated.

Determination of a therapeutically effective amount is well within the capability of those skilled in the art, especially in light of the disclosure provided herein.

Administration of the pharmaceutical composition of the invention can be performed prior to onset of a uterine hypercontractility disorder or manifestations associated therewith, at commencement of uterine hypercontractility disorder or manifestations associated therewith, during uterine hypercontractility disorder or manifestations associated therewith, or a combination thereof.

The exact formulation, route of administration and dosage can be chosen by the individual physician in view of the patient's condition. (See e.g., Fingl, et al., 1975, in "The Pharmacological Basis of Therapeutics", Ch. 1 p. 1).

The amount of a composition to be administered will be dependent on the subject being treated, for example, weight, age, and prior medical history, the severity of the uterine disorder, the route of administration, the judgment of the prescribing physician, etc.

EXAMPLE 1

Effect of S-Ethylisothiouronium Diethylphosphate on Uterine Abnormal Bleeding

Thirty-six women showing abnormal uterine bleeding were enrolled to this study. Each woman received one suppository of S-ethylisothiouronium diethylphosphate (100 mg of S-ethylisothiouronium diethylphosphate in 2 gr of Suppocire®, a suppository base obtained by esterification of hydrogenated palm oil and hydrogenated palm kelnel oil) per day, applied in the posterior vaginal fornix.

After administration of six suppositories of S-ethylisothiouronium diethylphosphate (100 mg each), applied intravaginally, complete disappearance of pathological uterine bleeding was obtained in 87.8% of cases (31 patients).

Haemostasis was obtained, on average, over the course of 40-58 hours from the start of treatment with S-ethylisothiouronium diethylphosphate in the form of vaginal suppositories. In 5 patients (12.2%) the intensity of bleeding was moderately reduced, but a full heornostatic effect was not reached. The majority (94.4%) of patients reported menstrual cycles with a normal duration and interval over the course of three consecutive months.

EXAMPLE 2

Effect of S-Ethylisothiouronium Diethylphosphate on Pain in Rats

The study was carried out on Wistar male rats (body weight of 210 g). The experiment was carried out on 30 rats divided into 3 groups of 10 animals each. The presence of pain was determined using the Tail-flick test, This method is based on monitoring the reaction time for the typical tail-withdrawal reflex as a result of thermal stimulation. First, the temperature (° C.) at which rat tails was withdrawn was determined, thus identifying the thermal level that caused pain. One hour later, the rats were injected intraperitoneally with S-ethylisothiouronium diethylphosphate in 0.9% NaCl. One group (10 rats) was injected with 5 mg/kg body weigh of S-ethylisothiouronium diethylphosphate, whilst the second and third groups (10 rats each) were injected with 10 and 20 mg/kg body weight, respectively.

The results indicated that the critical temperature at which untreated rats withdrew their tails was 73.15+1.09° C.

Intraperitoneal injection of 5 mg/kg S-ethylisothiouronium diethylphosphate increased the thermal level for tail withdrawal from 73+1.26° C. to 89.01+5.11° C., an increase of about 21%.

Injection of 10 mg/kg body weight of S-ethylisothiouronium diethylphosphate to rats increased the pain reception level under thermal stimulation from 73+3.63° C. to 96.4+ 3.98° C., an increase of about 31%.

Significant increase in the thermal reception was found in rats injected with 20 mg/kg body weight of S-ethylisothiouronium diethylphosphate. The pain reception level increased from 73.5±2.07 to 16.8±9.51° C. and represented 59% increase.

These results indicate that S-ethylisothiouronium diethylphosphate is a potent analgesic agent.

EXAMPLE 3

Effect of S-Ethylisothiouronium Diethylphosphate on Primary and Secondary Dysmenorrhea Vaginal suppositories containing S-ethylisothiouronium diethylphosphate (100 mg each/day) were applied to 28 women suffering from primary or secondary dysmenorrhea. Twenty-four hours after the beginning of the treatment, a significant decrease in the intensity of the pain in 60.7% of the cases (17 patients) was observed, while a complete disappearance of the pain in 11 patients (39.3%) was noted. Forty-eight hours after beginning of the treatment, i.e., after administering a second suppository containing S-ethylisothiouronium diethylphosphate, the pain was fully eradicated in all treated women.

EXAMPLE 4

Effect of S-Ethylisothiouronium Diethylphosphate on Abnormal Uterine Bleeding in Women Having Uterine Myomas and on Pelvic Pains in Women Having Primary Dysmenorrhea Sixty-ninewomen having symptomatic uterine myoma or primary dysmenorrhea were enrolled to this study. The women were treated with vaginal suppositories of S-ethylisothiouronium diethylphosphate (100 mg of S-ethylisothiouronium diethylphosphate in 2 gr of Suppocire® per day, applied in the posterior vaginal fornix).

The effect of S-ethylisothiouronium diethylphosphate on abnormal uterine bleeding was evaluated in 31 women patients (group I) having uterine myoma accompanied by pathological uterine hemorrhages. The average age of the patients was 42.3±4.3 years. All of these patients underwent 3-6 months before enrolling to the study uterine curettage, which had excluded the presence of a malignant process.

In addition, the effect of S-ethylisothiouronium diethylphosphate on pelvic pains was evaluated in 38 women patients having primary dysmenorrhea (group II). The average age of the patients was 24.8±4.1 years. All the 38 patients had experienced at least 6 painful menstrual cycles prior to their inclusion in the study. The duration of the menstrual cycle in all cases was normal, i.e., of 21-35 days, with the menstruation lasting 3-7 days. Further, none of the patients was treated with oral contraceptives for at least 6 months before enrollment. The patients were eligible for the study following the confirmation of normal hematological and biochemical indexes and exclusion of antecedent gynecological surgical procedures.

All of the patients of the study underwent an ecographic examination of the organs of the small pelvis.

In the patients of group I, the ecographic examination enabled determining the amount, dimension and localization of the myomatous nodules. Thus, the ultrasound gynecological (USG) examination recorded multiple myomatous nodules in 17 patients (54.8%), the presence of one single tumor in 11 patients (35.5%), and a diffuse uterine myoma in 3 cases (9.7%). Interstitial myoma was established in 25 cases (80.6%), and a subserous one in 6 cases (19.4%). The diameter of the nodules varied from 14 mm to 58 mm, measuring on average 28.9 mm. The uterine volume varied from 8 s.a to 12 s.a. The duration of the uterine hemorrhages varied from 2 to 14 days, lasting on average 6.3 days. The number of hygienic packets used daily by the patients varied from 2 to 8, amounting on average to about 5.6 packets.

In the patients of group II, the ecographic examination excluded the presence of a pathological process in the organs of the small pelvis and confirmed the diagnosis of primary dysmenonthea.

The effect of S-ethylisothiouronium diethylphosphate vaginal suppository, designated herein below Raviset, on uterine hemorrhage was established on the basis of the patients' condition (every 24 hours), subjective indexes obtained from the patients' reports, and on the basis of clinical and laboratory data.

Thus, the hemodynamic indexes (pulse, TA), Hb concentration and the Er number in peripheral blood were monitored. Subjective indexes of uterine hemorrhage in patients having uterine myoma included the intensity of uterine hemorrhage and the volume of blood lost. The answers were noted, using one of the following terms: complete disappearance of the hemorrhage, slight decrease of the bleeding, marked decrease of the bleeding, and absence of any effect due to the treatment.

To evaluate the intensity of pain, the patients reported the pain intensity at the beginning of the study, during, and at the termination of the medical management using one of the following terms: absence of pain; greatly diminished pain; slightly diminished pain; similar pain as of the previous treatment; and intensification of pain. The patients were requested to provide this assessment at the time of the treatment at 24-hour intervals, as well as to compare the severity of the pain with that of the previous treatment..

Possible adverse effects were explained to the patients, and informed consent was obtained from all of the female patients.

Raviset was inserted into the posterior vaginal fornix every 24 hours, for 4-5 days.

Results

In the first group of patients, the pulse was 81.3±3.9 strokes per minute, whereas the average pressure values were 108.9±8.3 mmHg for systolic blood pressure and 69.3±7 7 mmHg for diastolic pressure. In 11 patients (35.5%), change in blood pressure (TAs 98.0±5.9 mmHg and TAd 62.8±3.4 mmHg), accompanied by relative tachycardia (84.6±3.47 b/min) was monitored. In all other patients, the values of the hemodynamic indexes were within the normal range. In 22 patients (70,96%), the presence of anemia, with average values of hemoglobin concentration standing at 103.1±8.4 g/l and number of erythrocyts standing at 3.4±0.18 mln/mm³ was established.

In the second group of patients, the pulse was 78.8±4.2 strokes per minute, whereas the average pressure values were 123.4±6.3 mmHg for systolic blood pressure and 70.5±8.2 mmHg for diastolic pressure. The values of the hemodynamic indexes were, thus, within the normal range in all of the patients included in the study. The electrocardiogram did not record significant modification in the conducting system of the heart.

In group I, 24 hours after the application of the first Raviset suppository, 6 patients (19.3%) attested to a marked reduction in uterine bleedings, whereas 17 patients (54.8%) reported a slight decrease of uterine bleedings. In 8 cases (25.8%), the intensity of the uterine hemorrhage was maintained at the same level, being comparable with that prevailing prior to starting the treatment. No patient complained of an intensification of the bleeding. In most patients, the values of the blood pressure increased by approximately 10-15 mm Hg and the pulse frequency was reduced by 5-10 strokes per minute.

Thus, after the first administration of the suppository, improved hemodynamic indexes were observed in most of the patients.

Forty-eight hours after the beginning of the treatment, the uterine bleedings ceased in 4 (12.9%) patients. Six (19.4%) women reported a marked decrease in the intensity of the uterine bleedings, and the other 16 women (51.6%)—a moderate decrease of the bleedings. In 5 cases (16.1%), the uterine bleedings were maintained on the initial level. The average values of the hernodynamic indexes were not considerably different from those of the preceding day.

Seventy-two hours after beginning of the treatment, pathological uterine bleedings were absent in 7 patients (22.5%), 15 patients (48.4%) reported a significant reduction of the intensity of the uterine hemorrhage, and only 5 (16.1%) women observed a slight decrease of the bleedings. In 4 cases (12.9%), the treatment turned out to be inefficient.

After the application of the $4^1$ suppository, pathological uterine bleedings were absent in 21 patients (67.7%), and after the application of the fifth suppository, uterine hemorrhages were absent in 27 patients (87.1%), Four patients (12.9%) reported persistent uterine hemorrhage, of which 2 patients reported positive dynamics, whereas for 2 patients (6.5%) the treatment turned out to be inefficient.

The study established that after administration of 5 Raviset suppositories, uterine bleedings ceased in 27 of the 31 patients, Analysis of the clinical and paraclinical indices 24 hours after the cessation of the treatment, recorded alongside the improvement in the patients' condition and in the hemodynamic parameters (Ps decreased by 5.78 b/min; systolic TA increased on average by 8.76 mmHg, and the diastolic pressure—by 6.5 mmHg) showed an increase in hemoglobin concentration in the peripheral blood to 10.7 g/l on average, as well as an increase in the number of erythrocytes by 0.2 mil/mm³.

In group II, the treatment with Raviset significantly reduced the incidence and intensity of dysmenorrhea. The administration of 4 Raviset suppositories abrogated dysmenorrhea in 36 patients (94.7%).

Complications or severe adverse effects at the time of administering Raviset have not been established. The local tolerability and acceptability of the treatment was good in all cases.

Thus, this study showed that treatment with vaginal Raviset suppositories constitutes an efficient medicinal alternative for preventing and diminishing menstrual pain. The results of the study further showed that administration of Raviset is an efficient method in the treatment of pathological uterine bleedings in patients suffering from uterine myoma.

It is thus that the high therapeutic efficiency of the Raviset suppository, its cost effectiveness along with good local tolerability make the Raviset preparation a highly useful tool in gynecological practice.

It will be appreciated by persons skilled in the art that the present invention is not limited by what has been particularly shown and described herein above. Rather the scope of the invention is defined by the claims that follow.

What is claimed is:

1. A method for treating uterine bleeding, uterine cramping, and uterine contractions due to dysmenorrhea comprising administering to a woman in need of such treatment a pharmaceutical composition comprising a therapeutically effective amount of 100 to 200 mg S-ethylisothiouronium diethylphosphate once a day for one to six days to reduce the severity, duration or frequency of abnormal uterine bleeding and also to reduce or eliminate such uterine cramping and uterine contractions without impairing the woman's fertility or ability to conceive, wherein administration of the pharmaceutical composition is commenced prior to onset of menstruation or prior to the first occurrence of uterine bleeding, uterine cramping, and uterine contractions, wherein the woman in need of treatment is selected from the group consisting of fertile women and women who wish to conceive, and wherein said woman avoids or is recommended to avoid NSAIDs and contraceptives.

2. The method according to claim 1, wherein the pharmaceutical composition is formulated in a form selected from the group consisting of a solution, suspension, emulsion, tablet, capsule, powder, vaginal suppository, vaginal ring, vaginal pessary, vaginal tampon, implant, spray, cream, gel, ointment, and a sustained-release formulation.

3. The method according to claim 1, wherein the pharmaceutical composition is formulated as a vaginal suppository.

4. The method according to claim 1, wherein the therapeutically effective amount of S-ethylisothiouronium diethylphosphate is 100 mg.

5. The method according to claim 1, wherein dysmenorrhea is selected from the group consisting of primary dysmenorrhea and secondary dysmenorrhea.

6. The method according to claim 1, wherein the pharmaceutical composition comprises one or more natural, synthetic or partially synthetic fats or waxes.

7. The method according to claim 6, wherein the fats or waxes are selected from the group consisting of olive oil, corn oil, castor oil, hydrogenated oils, petrolatum, solid paraffin, liquid paraffin, carnauba wax, bees wax, lanolin, partially or totally synthetic esters of glycerol fatty acid, and mono, di, or triglycerides of saturated or unsaturated fatty acids.

8. The method according to claim 6, wherein the pharmaceutical composition further comprises one or more of the following excipients: a stabilizer, a surfactant, a pigment, a pH modifier, and water.

9. The method according to claim 1, wherein the administration of the pharmaceutical composition is commenced prior to onset of menstruation.

10. The method according to claim 1, wherein the administration of the pharmaceutical composition is commenced prior to the first occurrence of uterine cramping, uterine bleeding, and uterine contractions.

11. A method for treating uterine bleeding, uterine cramping, and uterine contractions due to dysmenorrhea comprising administering to a woman in need of such treatment a sustained-release pharmaceutical composition comprising a therapeutically effective amount of 100 to 200 mg S-ethylisothiouronium diethylphosphate, one or more natural, synthetic or partially synthetic fats or waxes, and one or more of the following excipients: a stabilizer, a surfactant, a pigment, a pH modifier, and water, wherein the pharmaceutical composition is administered once a day for one to six days to reduce the severity, duration or frequency of abnormal uterine bleeding and also to reduce or eliminate such uterine cramping and uterine contractions without impairing the woman's fertility or ability to conceive, wherein administration is commenced prior to onset of menstruation or prior to the first occurrence of uterine bleeding, uterine cramping, and uterine contractions, wherein the woman in need of treatment is selected from the group consisting of fertile women and women who wish to conceive, and wherein said woman avoids or is recommended to avoid NSAIDs and contraceptives.

12. The method according to claim 11, wherein the sustained-release pharmaceutical composition is in the form of a vaginal suppository, vaginal ring, vaginal pessary or vaginal tampon.

13. The method according to claim 11, wherein the administration of the pharmaceutical composition is commenced prior to onset of menstruation.

14. The method according to claim 11, wherein the administration of the pharmaceutical composition is commenced prior to the first occurrence of uterine cramping, uterine bleeding, and uterine contractions.

15. The method of claim 3, wherein the vaginal suppository is administered every 24 hours for 4 to 5 days.

16. The method of claim 11, wherein the pharmaceutical composition is formulated as a vaginal suppository and the vaginal suppository is administered every 24 hours for 4 to 5 days.

17. A method for treating uterine bleeding, uterine cramping, and uterine contractions due to dysmenorrhea comprising administering intravaginally to a woman in need of such treatment a pharmaceutical composition comprising a therapeutically effective amount of 100 to 200 mg S-ethylisothiouronium diethylphosphate once a day for one to six days to reduce the severity, duration or frequency of abnormal uterine bleeding and also to reduce or eliminate such uterine cramping and uterine contractions without impairing the woman's fertility or ability to conceive, wherein administration of the pharmaceutical composition is commenced prior to onset of menstruation or prior to the first occurrence of uterine bleeding, uterine cramping, and uterine contractions, wherein the woman in need of treatment is selected from the group consisting of fertile women and women who wish to conceive, and wherein said woman avoids or is recommended to avoid NSAIDs and contraceptives.

18. The method of claim 17, wherein the pharmaceutical composition is administered every 24 hours for 4 to 5 days.

19. The method according to claim 18, wherein the therapeutically effective amount of S-ethylisothiouronium diethylphosphate is 100 mg.

* * * * *